(12) United States Patent
Romesburg

(10) Patent No.: US 10,966,662 B2
(45) Date of Patent: Apr. 6, 2021

(54) MOTION-DEPENDENT AVERAGING FOR PHYSIOLOGICAL METRIC ESTIMATING SYSTEMS AND METHODS

(71) Applicant: Valencell, Inc., Raleigh, NC (US)

(72) Inventor: Eric Douglas Romesburg, Chapel Hill, NC (US)

(73) Assignee: Valencell, Inc., Raleigh, NC (US)

( * ) Notice: Subject to any disclaimer, the term of this patent is extended or adjusted under 35 U.S.C. 154(b) by 450 days.

(21) Appl. No.: 15/643,965

(22) Filed: Jul. 7, 2017

(65) Prior Publication Data

US 2018/0008200 A1 Jan. 11, 2018

Related U.S. Application Data

(60) Provisional application No. 62/359,962, filed on Jul. 8, 2016.

(51) Int. Cl.
*A61B 5/00* (2006.01)
*A61B 5/0205* (2006.01)
(Continued)

(52) U.S. Cl.
CPC ............ *A61B 5/721* (2013.01); *A61B 5/0205* (2013.01); *A61B 5/6803* (2013.01); *A61B 5/6815* (2013.01); *A61B 5/6898* (2013.01); *A61B 5/725* (2013.01); *A61B 5/7253* (2013.01); *A61B 5/02255* (2013.01); *A61B 5/02427* (2013.01); *A61B 5/0816* (2013.01); *A61B 5/1118* (2013.01); *A61B 5/14532* (2013.01);
(Continued)

(58) Field of Classification Search
CPC .......... A61B 5/721; A61B 5/723; A61B 5/725
See application file for complete search history.

(56) References Cited

U.S. PATENT DOCUMENTS 3,595,219 A 7/1971 Friedlander et al.
4,240,882 A 12/1980 Ang et al.
(Continued)

FOREIGN PATENT DOCUMENTS

AU 2015101130 10/2015
CN 101212927 7/2008
(Continued)

OTHER PUBLICATIONS

Fukushima et al. "Estimating Heart Rate using Wrist-type Photoplethysmography and Acceleration sensor while running" 2012 Annual International Conference of the IEEE Engineering in Medicine and Biology Society (pp. 2901-2904) (Sep. 2012).
(Continued)

*Primary Examiner* — Gary Jackson
*Assistant Examiner* — Anant A Gupta
(74) *Attorney, Agent, or Firm* — Myers Bigel, P.A.

(57) ABSTRACT

Physiological signal processing systems include a photoplethysmograph (PPG) sensor that is configured to generate a physiological waveform, and an inertial sensor that is configured to generate a motion signal. A physiological metric extractor is configured to extract a physiological metric from the physiological waveform that is generated by the PPG sensor. The physiological metric extractor includes an averager that has an impulse response that is responsive to the strength of the motion signal. Related methods are also described.

26 Claims, 7 Drawing Sheets

(51) Int. Cl.

| | | |
|---|---|---|
| G16H 40/63 | (2018.01) | |
| A61B 5/0225 | (2006.01) | |
| A61B 5/024 | (2006.01) | |
| A61B 5/08 | (2006.01) | |
| A61B 5/11 | (2006.01) | |
| A61B 5/145 | (2006.01) | |
| A61B 5/1455 | (2006.01) | |

(52) U.S. Cl.
CPC ......... *A61B 5/14552* (2013.01); *A61B 5/4866* (2013.01); *A61B 2562/0219* (2013.01); *A61B 2562/0238* (2013.01); *G16H 40/63* (2018.01)

(56) References Cited

U.S. PATENT DOCUMENTS

| | | |
|---|---|---|
| 4,281,645 A | 8/1981 | Jobsis |
| 4,331,154 A | 5/1982 | Broadwater et al. |
| 4,371,406 A | 2/1983 | Li |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,586,513 A | 5/1986 | Hamaguri |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,952,890 A | 8/1990 | Swanson |
| 4,952,928 A | 8/1990 | Carroll et al. |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,139,025 A | 8/1992 | Lewis et al. |
| 5,143,078 A | 9/1992 | Mather et al. |
| 5,226,417 A | 7/1993 | Swedlow et al. |
| 5,237,994 A | 8/1993 | Goldberger |
| 5,299,570 A | 4/1994 | Hatschek |
| 5,348,002 A | 9/1994 | Caro |
| 5,377,100 A | 12/1994 | Pope et al. |
| 5,386,819 A | 2/1995 | Kaneko et al. |
| 5,431,170 A | 7/1995 | Mathews |
| 5,448,082 A | 9/1995 | Kim |
| 5,482,036 A | 1/1996 | Diab et al. |
| 5,492,129 A | 2/1996 | Greenberger |
| 5,494,043 A | 2/1996 | O'Sullivan et al. |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,817,008 A | 10/1998 | Rafert et al. |
| 5,820,560 A | 10/1998 | Sinderby et al. |
| 5,846,190 A | 12/1998 | Woehrle |
| 5,853,005 A | 12/1998 | Scanlon |
| 5,904,654 A | 5/1999 | Wohltmann et al. |
| 5,938,593 A | 8/1999 | Ouellette |
| 5,954,644 A | 9/1999 | Dettling et al. |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,006,119 A | 12/1999 | Soller et al. |
| 6,013,007 A | 1/2000 | Root et al. |
| 6,022,748 A | 2/2000 | Charych et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,122,042 A | 9/2000 | Wunderman et al. |
| 6,148,229 A | 11/2000 | Morris, Sr. et al. |
| 6,155,983 A | 12/2000 | Kosuda et al. |
| 6,168,567 B1 | 1/2001 | Pickering et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,267,721 B1 | 7/2001 | Welles |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,608,562 B1 | 8/2003 | Kimura et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,702,752 B2 | 3/2004 | Dekker |
| 6,725,072 B2 | 4/2004 | Steuer et al. |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,954,644 B2 | 10/2005 | Johansson et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Romhild |
| 7,034,694 B2 | 4/2006 | Yamaguchi et al. |
| 7,039,454 B1 | 5/2006 | Kaga et al. |
| 7,041,062 B2 | 5/2006 | Friedrichs et al. |
| 7,043,287 B1 | 5/2006 | Khalil et al. |
| 7,048,687 B1 | 5/2006 | Reuss et al. |
| 7,054,674 B2 | 5/2006 | Cane et al. |
| 7,088,234 B2 | 8/2006 | Naito et al. |
| 7,107,088 B2 | 9/2006 | Aceti |

(56) References Cited

U.S. PATENT DOCUMENTS

| | | |
|---|---|---|
| 7,113,815 B2 | 9/2006 | O'Neil et al. |
| 7,117,032 B2 | 10/2006 | Childre et al. |
| 7,144,375 B2 | 12/2006 | Kosuda |
| 7,163,512 B1 | 1/2007 | Childre et al. |
| 7,175,601 B2 | 2/2007 | Verjus et al. |
| 7,190,986 B1 | 3/2007 | Hannula et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo |
| 7,341,559 B2 | 3/2008 | Schulz et al. |
| 7,376,451 B2 | 5/2008 | Mahony et al. |
| 7,378,954 B2 | 5/2008 | Wendt |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,620,450 B2 | 11/2009 | Kim et al. |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar, Jr. et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | Leboeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | Leboeuf et al. |
| 8,233,955 B2 | 7/2012 | Al-Ali et al. |
| 8,251,903 B2 | 8/2012 | Leboeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | Leboeuf et al. |
| 8,323,982 B2 | 12/2012 | Leboeuf et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | Leboeuf et al. |
| 8,647,270 B2 | 2/2014 | Leboeuf et al. |
| 8,652,040 B2 | 2/2014 | Leboeuf et al. |
| 8,652,409 B2 | 2/2014 | Leboeuf et al. |
| 8,679,008 B2 | 3/2014 | Hughes et al. |
| 8,700,111 B2 | 4/2014 | Leboeuf et al. |
| 8,702,607 B2 | 4/2014 | Leboeuf et al. |
| 8,730,048 B2 | 5/2014 | Shen et al. |
| 8,788,002 B2 | 7/2014 | Leboeuf et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,961,415 B2 | 2/2015 | Leboeuf et al. |
| 8,996,332 B2 * | 3/2015 | Kahn ................ A61B 5/1123 |
| | | 702/141 |
| 9,005,129 B2 | 4/2015 | Venkatraman et al. |
| 9,044,180 B2 | 6/2015 | Leboeuf et al. |
| 9,289,175 B2 | 3/2016 | Leboeuf et al. |
| 9,801,552 B2 | 10/2017 | Romesburg |
| 9,808,204 B2 | 11/2017 | Leboeuf et al. |
| 9,943,266 B2 * | 4/2018 | Adams ................ A61B 5/721 |
| 2001/0015123 A1 | 8/2001 | Nishitani et al. |
| 2001/0044588 A1 | 11/2001 | Mault |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0173780 A1 | 11/2002 | Altshuler et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0065269 A1 | 4/2003 | Vetter et al. |
| 2003/0083583 A1 | 5/2003 | Kovtun et al. |
| 2003/0109030 A1 | 6/2003 | Uchida et al. |
| 2003/0109791 A1 | 6/2003 | Kondo et al. |
| 2003/0130586 A1 | 7/2003 | Starobin et al. |
| 2003/0181795 A1 | 9/2003 | Suzuki et al. |
| 2003/0181798 A1 | 9/2003 | Al-Ali |
| 2003/0181817 A1 | 9/2003 | Mori |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2003/0233051 A1 | 12/2003 | Verjus et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0039254 A1 | 2/2004 | Stivoric et al. |
| 2004/0073455 A1 | 4/2004 | McConnochie et al. |
| 2004/0075677 A1 | 4/2004 | Loyall et al. |
| 2004/0077934 A1 | 4/2004 | Massad |
| 2004/0081621 A1 | 4/2004 | Arndt et al. |
| 2004/0082842 A1 | 4/2004 | Lumba et al. |
| 2004/0097796 A1 | 5/2004 | Berman et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0158167 A1 | 8/2004 | Smith et al. |
| 2004/0186387 A1 | 9/2004 | Kosuda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0228494 A1 | 11/2004 | Smith |
| 2004/0242976 A1 | 12/2004 | Abreu |
| 2004/0254501 A1 | 12/2004 | Mault |
| 2005/0004458 A1 | 1/2005 | Kanayama et al. |
| 2005/0007582 A1 | 1/2005 | Villers et al. |
| 2005/0021519 A1 | 1/2005 | Ghouri |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0036212 A1 | 2/2005 | Saito |
| 2005/0038349 A1 | 2/2005 | Choi et al. |
| 2005/0043630 A1 | 2/2005 | Buchert |
| 2005/0059870 A1 | 3/2005 | Aceti |
| 2005/0070809 A1 | 3/2005 | Acres |
| 2005/0084666 A1 | 4/2005 | Pong et al. |
| 2005/0100866 A1 | 5/2005 | Arnone et al. |
| 2005/0101845 A1 | 5/2005 | Nihtila |

(56) References Cited

U.S. PATENT DOCUMENTS

| | | |
|---|---|---|
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0212405 A1 | 9/2005 | Negley |
| 2005/0222487 A1 | 10/2005 | Miller, III et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0228463 A1 | 10/2005 | Mac et al. |
| 2005/0240087 A1 | 10/2005 | Keenan et al. |
| 2005/0245839 A1 | 11/2005 | Stivoric et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0074333 A1 | 4/2006 | Huiku |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0287590 A1 | 12/2006 | McEowen |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0060819 A1 | 3/2007 | Altshuler et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0118054 A1 | 5/2007 | Pinhas et al. |
| 2007/0135717 A1 | 6/2007 | Uenishi et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0001735 A1 | 1/2008 | Tran |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0081972 A1 | 4/2008 | Debreczeny |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0133699 A1 | 6/2008 | Craw et al. |
| 2008/0141301 A1 | 6/2008 | Azzaro et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221414 A1 | 9/2008 | Baker, Jr. |
| 2008/0221461 A1 | 9/2008 | Zhou et al. |
| 2008/0249594 A1 | 10/2008 | Dietrich et al. |
| 2008/0287752 A1 | 11/2008 | Stroetz et al. |
| 2008/0312517 A1 | 12/2008 | Genoe et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0010556 A1 | 1/2009 | Uchibayashi et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0112101 A1 | 4/2009 | Furness, III et al. |
| 2009/0131761 A1 | 5/2009 | Moroney, III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0281435 A1 | 11/2009 | Ahmed et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney, III et al. |
| 2010/0185105 A1 | 7/2010 | Baldinger |
| 2010/0217100 A1 | 8/2010 | Leboeuf et al. |
| 2010/0217102 A1 | 8/2010 | Leboeuf et al. |

(56) References Cited

U.S. PATENT DOCUMENTS

| | | |
|---|---|---|
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2011/0028810 A1 | 2/2011 | Van Slyke et al. |
| 2011/0028813 A1 | 2/2011 | Watson et al. |
| 2011/0066007 A1* | 3/2011 | Banet .............. A61B 5/0402 600/301 |
| 2011/0081037 A1 | 4/2011 | Oh et al. |
| 2011/0098112 A1 | 4/2011 | Leboeuf et al. |
| 2011/0105869 A1 | 5/2011 | Wilson et al. |
| 2011/0112382 A1 | 5/2011 | Li et al. |
| 2011/0130638 A1 | 6/2011 | Raridan |
| 2011/0142371 A1 | 6/2011 | King et al. |
| 2011/0178564 A1 | 7/2011 | Keefe |
| 2011/0288379 A1 | 11/2011 | Wu |
| 2012/0030547 A1 | 2/2012 | Raptis et al. |
| 2012/0095303 A1 | 4/2012 | He |
| 2012/0150052 A1 | 6/2012 | Buchheim et al. |
| 2012/0156933 A1 | 6/2012 | Kreger et al. |
| 2012/0172702 A1* | 7/2012 | Koyrakh .............. A61B 5/721 600/408 |
| 2012/0179011 A1 | 7/2012 | Moon et al. |
| 2012/0190948 A1* | 7/2012 | Vetter .............. A61B 5/14552 600/324 |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0277548 A1 | 11/2012 | Burton |
| 2012/0296184 A1 | 11/2012 | Leboeuf et al. |
| 2013/0053661 A1 | 2/2013 | Alberth et al. |
| 2013/0072765 A1 | 3/2013 | Kahn et al. |
| 2013/0197377 A1 | 8/2013 | Kishi et al. |
| 2013/0245387 A1 | 9/2013 | Patel |
| 2013/0336495 A1 | 12/2013 | Burgett et al. |
| 2014/0012105 A1 | 1/2014 | Leboeuf et al. |
| 2014/0051940 A1 | 2/2014 | Messerschmidt |
| 2014/0051948 A1 | 2/2014 | Leboeuf et al. |
| 2014/0052567 A1 | 2/2014 | Bhardwaj et al. |
| 2014/0058220 A1 | 2/2014 | Leboeuf et al. |
| 2014/0073486 A1 | 3/2014 | Ahmed et al. |
| 2014/0088433 A1 | 3/2014 | Shan |
| 2014/0094663 A1 | 4/2014 | Leboeuf et al. |
| 2014/0100432 A1 | 4/2014 | Golda et al. |
| 2014/0114147 A1 | 4/2014 | Romesburg |
| 2014/0127996 A1 | 5/2014 | Park et al. |
| 2014/0128690 A1 | 5/2014 | Leboeuf |
| 2014/0135596 A1 | 5/2014 | Leboeuf et al. |
| 2014/0140567 A1 | 5/2014 | Leboeuf et al. |
| 2014/0171755 A1* | 6/2014 | LeBoeuf .............. A61B 5/021 600/301 |
| 2014/0213863 A1 | 7/2014 | Loseu et al. |
| 2014/0219467 A1 | 8/2014 | Kurtz |
| 2014/0228649 A1 | 8/2014 | Rayner et al. |
| 2014/0235967 A1 | 8/2014 | Leboeuf et al. |
| 2014/0235968 A1 | 8/2014 | Leboeuf et al. |
| 2014/0236531 A1 | 8/2014 | Carter |
| 2014/0243617 A1 | 8/2014 | Leboeuf et al. |
| 2014/0243620 A1 | 8/2014 | Leboeuf et al. |
| 2014/0275852 A1 | 9/2014 | Hong et al. |
| 2014/0275854 A1 | 9/2014 | Venkatraman et al. |
| 2014/0275855 A1 | 9/2014 | Leboeuf et al. |
| 2014/0276119 A1 | 9/2014 | Venkatraman et al. |
| 2014/0287833 A1 | 9/2014 | Leboeuf et al. |
| 2014/0288392 A1 | 9/2014 | Hong et al. |
| 2014/0288396 A1 | 9/2014 | Leboeuf et al. |
| 2014/0288436 A1 | 9/2014 | Venkatraman et al. |
| 2014/0323829 A1 | 10/2014 | Leboeuf et al. |
| 2014/0323830 A1 | 10/2014 | Leboeuf et al. |
| 2014/0323880 A1 | 10/2014 | Ahmed et al. |
| 2014/0327515 A1* | 11/2014 | Luna .............. A61B 5/0535 340/4.42 |
| 2014/0378844 A1 | 12/2014 | Fei |
| 2015/0011898 A1 | 1/2015 | Romesburg |
| 2015/0018636 A1* | 1/2015 | Romesburg .............. A61B 5/024 600/301 |
| 2015/0025393 A1 | 1/2015 | Hong et al. |
| 2015/0031967 A1 | 1/2015 | Leboeuf et al. |
| 2015/0032009 A1 | 1/2015 | Leboeuf et al. |
| 2015/0057967 A1 | 2/2015 | Albinali |
| 2015/0080741 A1 | 3/2015 | Leboeuf et al. |
| 2015/0080746 A1 | 3/2015 | Bleich et al. |
| 2015/0157269 A1* | 6/2015 | Lisogurski .............. A61B 5/0205 600/301 |
| 2015/0190085 A1 | 7/2015 | Nathan et al. |
| 2015/0196256 A1 | 7/2015 | Venkatraman et al. |
| 2015/0250396 A1 | 9/2015 | Ahmed et al. |
| 2015/0265217 A1 | 9/2015 | Penders et al. |
| 2015/0282768 A1 | 10/2015 | Luna et al. |
| 2015/0289820 A1 | 10/2015 | Miller et al. |
| 2015/0305682 A1 | 10/2015 | Leboeuf et al. |
| 2015/0342481 A1 | 12/2015 | Liu et al. |
| 2015/0366509 A1 | 12/2015 | Romesburg |
| 2016/0022220 A1 | 1/2016 | Lee et al. |
| 2016/0029964 A1 | 2/2016 | Leboeuf et al. |
| 2016/0038045 A1* | 2/2016 | Shapiro .............. A61B 5/02416 600/479 |
| 2016/0051157 A1 | 2/2016 | Waydo |
| 2016/0089033 A1 | 3/2016 | Saponas et al. |
| 2016/0089086 A1* | 3/2016 | Lin .............. A61B 5/721 600/479 |
| 2016/0094899 A1 | 3/2016 | Aumer et al. |
| 2016/0120476 A1* | 5/2016 | Liu .............. A61B 5/721 600/479 |
| 2016/0206247 A1 | 7/2016 | Morland et al. |
| 2016/0287108 A1 | 10/2016 | Wei et al. |
| 2016/0361021 A1 | 12/2016 | Salehizadeh et al. |
| 2017/0007166 A1 | 1/2017 | Roovers et al. |
| 2017/0034615 A1 | 2/2017 | Mankodi et al. |
| 2017/0112447 A1 | 4/2017 | Aumer et al. |
| 2017/0232294 A1* | 8/2017 | Kruger .............. G06F 19/00 434/247 |
| 2017/0290549 A1 | 10/2017 | Romesburg |
| 2018/0020979 A1 | 1/2018 | Wagner et al. |
| 2018/0049645 A1 | 2/2018 | Romesburg |
| 2018/0146926 A1* | 5/2018 | Ishikawa .............. A61B 5/02 |

FOREIGN PATENT DOCUMENTS

| | | |
|---|---|---|
| CN | 201438747 | 4/2010 |
| DE | 3910749 | 10/1990 |
| EP | 1297784 | 4/2003 |
| EP | 1480278 | 11/2004 |
| EP | 1908401 A1 | 4/2008 |
| EP | 2077091 | 7/2009 |
| EP | 2182839 | 5/2010 |
| EP | 2667769 A2 | 12/2013 |
| GB | 2408209 | 5/2005 |
| GB | 2411719 | 9/2005 |
| JP | 07241279 | 9/1995 |
| JP | 09253062 | 9/1997 |
| JP | 09299342 | 11/1997 |
| JP | 2000-116611 | 4/2000 |
| JP | 2001-025462 | 1/2001 |
| JP | 2003-159221 | 6/2003 |
| JP | 2004-513750 | 5/2004 |
| JP | 2004-283523 | 10/2004 |
| JP | 2005-040261 | 2/2005 |
| JP | 2005-270544 | 10/2005 |
| JP | 2007-044203 | 2/2007 |
| JP | 2007-185348 | 7/2007 |
| JP | 2008-136556 | 6/2008 |
| JP | 2008-279061 | 11/2008 |
| JP | 2009-153664 | 7/2009 |
| JP | 2010-526646 | 8/2010 |
| JP | 2014-068733 | 4/2014 |
| KR | 20-0204510 | 11/2000 |
| WO | 00/24064 | 4/2000 |

(56) References Cited

FOREIGN PATENT DOCUMENTS

| WO | 00/47108 | 8/2000 |
|---|---|---|
| WO | 01/08552 | 2/2001 |
| WO | 02/17782 | 3/2002 |
| WO | 2005/010568 | 2/2005 |
| WO | 2005/020121 | 3/2005 |
| WO | 2005/036212 | 4/2005 |
| WO | 2005/110238 | 11/2005 |
| WO | 2006/009830 | 1/2006 |
| WO | 2006/067690 | 6/2006 |
| WO | 2007/012931 | 2/2007 |
| WO | 2007/053146 | 5/2007 |
| WO | 2008/141306 | 11/2008 |
| WO | 2011/127063 | 10/2011 |
| WO | 2013/019494 | 2/2013 |
| WO | 2013/038296 | 3/2013 |
| WO | 2013/109389 | 7/2013 |
| WO | 2013/109390 | 7/2013 |
| WO | 2014/092932 | 6/2014 |
| WO | 2014196119 | 12/2014 |
| WO | 2015/068066 | 5/2015 |
| WO | 2015/128226 | 9/2015 |
| WO | 2015/131065 | 9/2015 |
| WO | 2017/027551 | 2/2017 |

OTHER PUBLICATIONS

Asada et al. "Mobile Monitoring with Wearable Photoplethysmographic Biosensors" IEEE Engineering in Medicine and Biology Magazine (pp. 28-40) (May/Jun. 2003).

Bifulco et al. "Bluetooth Portable Device for Continuous ECG and Patient Motion Monitoring During Daily Life" Medicon 2007 IFMBE Proceedings 16:369-372 (2007).

Brodersen et al. "In-Ear Acquisition of Vital Signs Discloses New Chances for Preventive Continuous Cardiovascular Monitoring" 4th International Workshop on Wearable and Implantable Body Sensor Networks 13:189-194 (2007).

Celka et al. "Motion Resistant Earphone Located Infrared based Heart Rate Measurement Device" Proceedings of the Second IASTED International Conference on Biomedical Engineering (pp. 582-585) (Feb. 16-18, 2004).

Comtois "Implementation of Accelerometer-Based Adaptive Noise Cancellation in a Wireless Wearable Pulse Oximeter Platform for Remote Physiological Monitoring and Triage" Thesis, Worcester Polytechnic Institute (149 pages) (Aug. 31, 2007).

Comtois et al. "A Wearable Wireless Reflectance Pulse Oximeter for Remote Triage Applications" IEEE (pp. 53-54) (2006).

Comtois et al. "A Comparative Evaluation of Adaptive Noise Cancellation Algorithms for Minimizing Motion Artifacts in a Forehead-Mounted Wearable Pulse Oximeter" Proceedings of the 29th Annual International Conference of the IEEE EMBS (pp. 1528-1531) (Aug. 23-26, 2007).

Duun et al. "A Novel Ring Shaped Photodiode for Reflectance Pulse Oximetry in Wireless Applications" IEEE Sensors 2007 Conference (pp. 596-599) (2007).

FiTrainer "The Only Trainer You Need" http://itami.com © 2008 FiTrainer™ (2 pages) (Downloaded Feb. 26, 2010).

Fleming et al. "A Comparison of Signal Processing Techniques for the Extraction of Breathing Rate from the Photoplethysmorgram" World Academy of Science, Engineering and Technology 30:276-280 (Oct. 2007).

Geun et al. "Measurement Site and Applied Pressure Consideration in Wrist Photoplethysmography" The 23rd International Technical Conference on Circuits/Systems, Computers and Communications (pp. 1129-1132) (2008).

Gibbs et al. "Active motion artifact cancellation for wearable health monitoring sensors using collocated MEMS accelerometers" Proc. of SPIE Smart Structures and Materials, 2005: Sensors and Smart Structures Technologies for Civil, Mechanical, and Aerospace Systems 5765:811-819 (2005).

Gibbs et al. "Reducing Motion Artifact in Wearable Bio-Sensors Using MEMS Accelerometers for Active Noise Cancellation" 2005 American Control Conference 1581-1586 (Jun. 8-10, 2005).

Haahr et al. "A Wearable "Electronic Patch" for Wireless Continuous Monitoring of Chronically Diseased Patients" Proceedings of the 5th International Workshop on Wearable and Implantable Body Sensor Networks, in conjunction with the 5th International Summer School and Symposium on Medical Devices and Biosensors (pp. 66-70) (Jun. 1-3, 2008).

Han et al. "Artifacts in wearable photoplethysmographs during daily life motions and their reduction with least mean square based active noise cancellation method" Computers in Biology and Medicine 42:387-393 (Apr. 2012).

Han et al. "Development of a wearable health monitoring device with motion artifact reduced algorithm" International Conference on Control, Automation and Systems 2007 (ICCAS 2007) (pp. 1581-1584) (Oct. 17-20, 2007).

Jiang "Motion-Artifact Resistant Design of Photoplethysmograph Ring Sensor for Driver Monitoring" Thesis, Massachusetts Institute of Technology (62 pages) (Feb. 2004).

Kuzmina et al. "Compact multi-functional skin spectrometry set-up" Advanced Optical Materials, Technologies, and Devices, Proc. of SPIE 6596:65960T-1-65960T-6 (2007).

Lee et al. "A Mobile Care System With Alert Mechanism" IEEE Transactions on Information Technology in Biomedicine 11(5):507-517 (Sep. 2007).

Lee et al. "Respiratory Rate Detection Algorithms by Photoplethysmography Signal Processing" 30th Annual International IEEE EMBS Conference (pp. 1140-1143) (Aug. 20-24, 2008).

Lindberg et al. "Monitoring of respiratory and heart rates using a fibre-optic sensor" Med Biol Eng Comput 30(5):533-537 (Sep. 1992).

Luprano "Sensors and Parameter Extraction by Wearable Systems: Present Situation and Future" pHealth 2008 (29 pages) (May 21, 2008).

Lygouras et al. "Optical-Fiber Finger Photo-Plethysmograph Using Digital Techniques" IEEE Sensors Journal 2(1):20-25 (Feb. 2002).

Maguire et al. "The Design and Clinical Use of a Reflective Brachial Photoplethysmograph" Signals and Systems Research Group, National University of Ireland (13 pages) (Apr. 2002).

Mendelson et al. "Measurement Site and Photodetector Size Considerations in Optimizing Power Consumption of a Wearable Reflectance Pulse Oximeter" Proceedings of the 25th Annual International Conference of the IEEE EMBS (pp. 3016-3019) (Sep. 17-21, 2003).

Mendelson et al. "Noninvasive Pulse Oximetry Utilizing Skin Reflectance Photoplethysmography" IEEE Transactions on Biomedical Engineering 35(10):798-805 (Oct. 1988).

Nakajima et al. "Monitoring of heart and respiratory rates by photoplethysmography using a digital filtering technique" Med. Eng. Phys. 18(5):365-372 (Jul. 1996).

Notification of Transmittal of the International Search Report and the Written Opinion of the International Searching Authority, or the Declaration, in corresponding PCT Application No. PCT/US2017/041006 (15 pages) (dated Sep. 6, 2017).

Poh et al. "Motion Tolerant Magnetic Earring Sensor and Wireless Earpiece for Wearable Photoplethysmography" IEEE Transactions on Information Technology in Biomedicine 14(3):786-794 (May 2010).

Renevey et al. "Wrist-Located Pulse Detection Using IR Signals, Activity and Nonlinear Artifact Cancellation" IEEE EMBS (4 pages) (2001).

Rhee et al. "Artifact-Resistant Power-Efficient Design of Finger-Ring Plethysmographic Sensors" IEEE Transactions on Biomedical Engineering 48(7):795-805 (Jul. 2001).

Shaltis "Analysis and Validation of an Artifact Resistant Design for Oxygen Saturation Measurement Using Photo Plethysmographic Ring Sensors" Thesis, Massachusetts Institute of Technology (103 pages) (Jun. 2004).

Shaw et al. "Warfighter Physiological and Environmental Monitoring: A Study for the U.S. Army Research Institute in Environmental Medicine and the Soldier Systems Center" Massachusetts Institute of Technology Lincoln Laboratory (141 pages) (Nov. 1, 2004).

(56) References Cited

OTHER PUBLICATIONS

Shin et al. "A Novel Headset with a Transmissive PPG Sensor for Heart Rate Measurement" 13th International Conference on Biomedical Engineering (pp. 519-522) (2009).
Spigulis et al. "Wearable wireless photoplethysmography sensors" Proc. of SPIE 6991:69912O-1-69912O-7 (2008).
Takatani et al. "Optical Oximetry Sensors for Whole Blood and Tissue" IEEE Engineering in Medicine and Biology (pp. 347-357) (Jun./Jul. 1994).
Vogel et al. "A System for Assessing Motion Artifacts in the Signal of a Micro-Optic In-Ear Vital Signs Sensor" 30th Annual International IEEE EMBS Conference (Aug. 20-24, 2008).
Vogel et al. "In-Ear Heart Rate Monitoring Using a Micro-Optic Reflective Sensor" Proceedings of the 29th Annual International Conference of the IEEE EMBS Cite Internationale (pp. 1375-1378) (Aug. 23-26, 2007).
Wang et al. "Multichannel Reflective PPG Earpiece Sensor With Passive Motion Cancellation" IEEE Transactions on Biomedical Circuits and Systems 1(4):235-241 (Dec. 2007).
Wang et al. "Reflective Photoplethysmograph Earpiece Sensor for Ubiquitous Heart Rate Monitoring" 4th International Workshop on Wearable and Implantable Body Sensor Networks IFMBE Proceedings 13:179-183 (2007).
Webster, John G. "Design of Pulse Oximeters" Medical Science Series, Institute of Physics Publication (143 pages) (Aug. 1997).
Wei et al. "A New Wristband Wearable Sensor Using Adaptive Reduction Filter to Reduce Motion Artifact" Proceedings of the 5th International Conference on Information Technology and Application in Biomedicine, in conjunction with The 2nd International Symposium & Summer School on Biomedical and Health Engineering (pp. 278-281) (May 30-31, 2008).
Wikipedia "Least mean squares filter" Retrieved at URL: https://en.wikipedia.org/wiki/Least_mean_squares_filter (6 pages) (Retrieved on Mar. 17, 2016).
Wood "Motion Artifact Reduction for Wearable Photoplethysmogram Sensors Using Micro Accelerometers and Laguerre Series Adaptive Filters" Thesis, Massachusetts Institute of Technology (74 pages) (Jun. 2008).
Wood et al. "Active Motion Artifact Reduction for Wearable Sensors Using Laguerre Expansion and Signal Separation" Proceedings of the 2005 IEEE Engineering in Medicine and Biology 27th Annual Conference (pp. 3571-3574) (Sep. 1-4, 2005).

\* cited by examiner

MOTION-DEPENDENT AVERAGING FOR PHYSIOLOGICAL METRIC ESTIMATING SYSTEMS AND METHODS

CLAIM OF PRIORITY

This application claims priority from U.S. Provisional Patent Application No. 62/359,962 entitled "MOTION-DEPENDENT AVERAGING FOR PHYSIOLOGICAL METRIC ESTIMATING SYSTEMS AND METHODS" filed Jul. 8, 2016, in the United States Patent and Trademark Office, the disclosure of which is incorporated by reference herein in its entirety.

BACKGROUND

Various embodiments described herein relate generally to signal processing systems and methods, and more particularly to physiological signal processing systems and methods.

There is a growing market demand for personal health and environmental monitors, for example, for gauging overall health, fitness, metabolism, and vital status during exercise, athletic training, work, public safety activities, dieting, daily life activities, sickness and physical therapy. These personal health and environmental monitors process physiological signals that may be obtained from one or more physiological sensors, and are configured to extract one or more physiological metrics from physiological waveforms. Unfortunately, inaccurate physiological metric extraction can reduce the accuracy of health, fitness and/or vital status monitoring.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Various embodiments described herein can provide physiological signal processing systems that include a photoplethysmograph (PPG) sensor that is configured to generate a physiological waveform, and an inertial sensor that is configured to generate a motion signal. A physiological metric extractor is configured to extract a physiological metric from the physiological waveform that is generated by the PPG sensor. The physiological metric extractor includes an averager that has an impulse response that is responsive to the motion signal and, in some embodiments, to the strength of the motion signal.

Various embodiments of averagers may be provided according to various embodiments described herein. For example, the averager may operate in the time domain or in the frequency domain. The averager may include a spectral transformer or an averaging filter, such as an averaging window. Moreover, the impulse response may be responsive to the motion signal according to a discrete, continuous, linear and/or nonlinear function that may include hysteresis. The strength of the motion signal may comprise a maximum, sum of squares, maximum of squares, sum of absolute values, maximum of absolute values, root-sum-squares, root-mean-squares and/or decimation of a magnitude of the motion signal over a given time interval. Finally, the inertial sensor may comprise an accelerometer, an optical sensor, a blocked channel sensor, a capacitive sensor and/or a piezo sensor.

Various embodiments of a physiological metric extractor that includes an averager having an impulse response that is responsive to the motion signal will now be described. For example, in some embodiments, the impulse response has a first value in response to the strength of the motion signal exceeding a first threshold and a second value in response to the strength of the motion signal being less than a second threshold. The first value of the impulse response may set a first averaging window size of the averager and the second value of the impulse response may set a second averaging window size of the averager. Thus, the averaging window size of the averager may be a linear and/or nonlinear function of the strength of the motion signal. In other embodiments, the impulse response has a first value in response to the strength of the motion signal exceeding a first threshold but being less than a second threshold, a second value in response to the strength of the motion signal exceeding the second threshold but being less than a third threshold and a third value in response to the strength of the motion signal exceeding the third threshold. Thus, the first value of the impulse response may set a first averaging window size of the averager, the second value of the impulse response may set a second averaging window size of the averager and the third value of the impulse response may set a third averaging window size of the averager. Accordingly, two or more thresholds may be provided.

In other embodiments, the physiological metric extractor further comprises a spectral transformer that is configured to provide a weighted average spectral response over a window of samples that are derived from the physiological waveform that is generated by the PPG sensor. The weights and the number of samples in the window of samples define the impulse response.

In yet other embodiments, wherein a window size of the averager defines impulse response, the physiological metric extractor may further comprise a buffer configured to store a plurality of samples of the physiological waveform that is generated by the PPG sensor therein, ranging from a newest sample to an oldest sample. The buffer is further configured to store sufficient samples to correspond to a largest averaging window size.

The physiological metric may comprise a heart rate, respiration rate, heart rate variability (HRV), pulse pressure, systolic blood pressure, diastolic blood pressure, step rate, oxygen uptake ($VO_2$), maximal oxygen uptake ($VO_2$ max), calories burned, trauma, cardiac output and/or blood analyte levels including percentage of hemoglobin binding sites occupied by oxygen ($SPO_2$), percentage of methemoglobins, percentage of carbonyl hemoglobin and/or glucose level.

Moreover, in some embodiments, a portable housing may be provided, wherein the PPG sensor, the inertial sensor and the physiological metric extractor are all included in the portable housing. A physiological metric assessor also may be provided, within or external to the portable housing, that is responsive to the physiological metric extractor and that is configured to process the physiological metric to generate at-least-one physiological assessment. The at-least-one physiological assessment may include ventilatory threshold, lactate threshold, cardiopulmonary status, neurological status, aerobic capacity ($VO_2$ max) and/or overall health or fitness.

Other embodiments described herein may provide a physiological processing system for a physiological waveform that is generated by a PPG sensor and a motion signal. These physiological signal processing systems may include a physiological metric extractor that is configured to extract the physiological metric from the physiological waveform that is generated by the PPG sensor. The physiological metric extractor has an averaging window of size that is responsive to the motion signal. In some embodiments, the averaging window size is responsive to the strength of the motion signal, as was described above. In some embodiments, the averaging size may have a first value and a second value or more than two different values, depending on the strength of the motion signal and one or more thresholds. Moreover, the averaging window size may be a linear and/or nonlinear function of the strength of the motion signal. The averager may operate in a time domain or in the frequency domain. A buffer may also be provided, as was described above. Finally, a physiological metric assessor may be provided as was described above.

Various embodiments were described above in connection with physiological signal processing systems. However, analogous physiological signal processing methods may also be provided according to various embodiments described herein. For example, some embodiments described herein can provide a physiological signal processing method comprising setting an impulse response in response to a motion signal, averaging a physiological waveform that is generated by a PPG sensor based on the impulse response that was set, and extracting a physiological metric from the physiological waveform that was averaged. In some embodiments, the setting may comprise setting an impulse response in response to the strength of the motion signal according to any of the embodiments described above. Moreover, the impulse response may have first, second, third, etc. values, depending on the strength of the motion signal relative to one or more thresholds, and these values may set averaging window sizes of the averaging, as was described above. The physiological metric may also be processed to generate at-least-one physiological assessment, as was described above.

Yet other embodiments of physiological signal processing methods may comprise setting an averaging window size in response to a motion signal, averaging a physiological waveform that is generated by a PPG sensor based on the averaging window size that was set, and extracting a physiological metric from the physiological waveform that was averaged. Again, the signal strength may be obtained according to any of the embodiments described herein, and the setting may comprise setting an average window size in response to the strength of the motion signal based on a linear and/or nonlinear function and/or the value of the motion signal relative to one or more thresholds.

DETAILED DESCRIPTION

Figure 1:
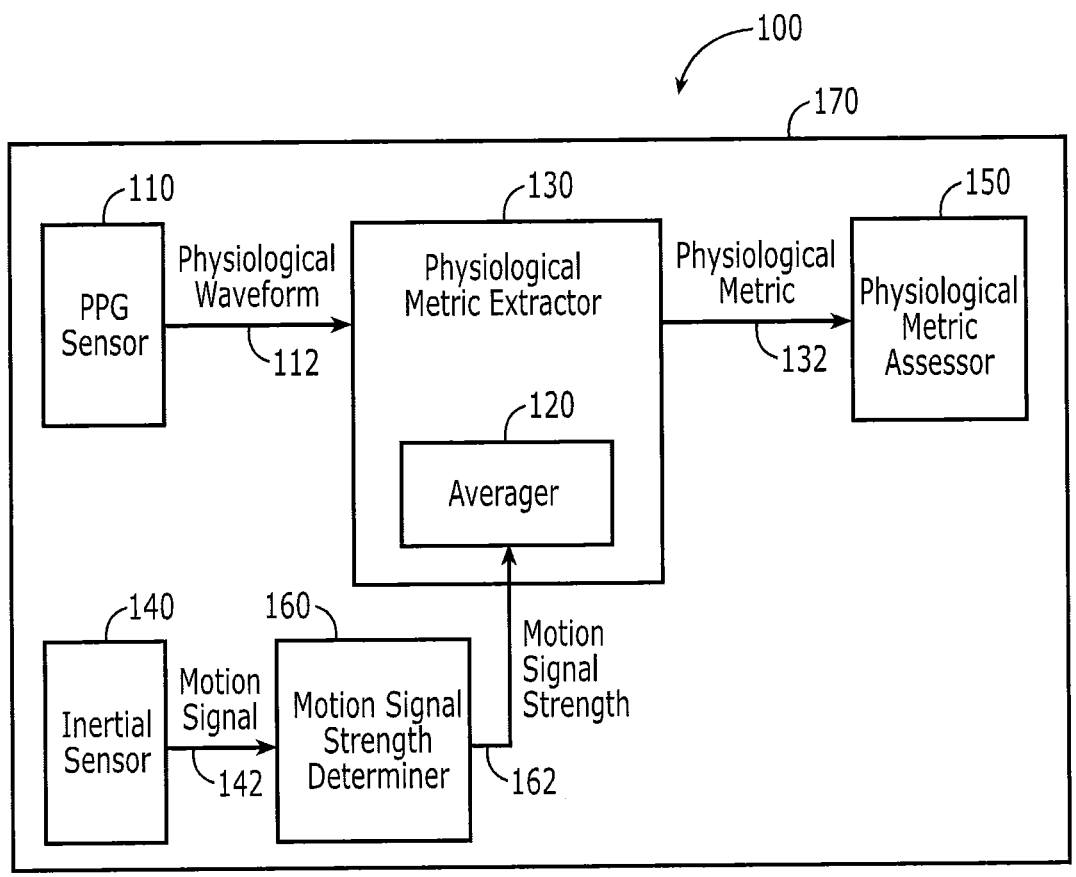
FIG. 1 is a functional block diagram of physiological signal processing systems and methods according to various embodiments described herein.

The present invention will now be described more fully hereinafter with reference to the accompanying figures, in which various embodiments are shown. This invention may, however, be embodied in many different forms and should not be construed as limited to the embodiments set forth herein. Like numbers refer to like elements throughout. The sequence of operations (or steps) is not limited to the order presented in the figures and/or claims unless specifically indicated otherwise. Features described with respect to one figure or embodiment can be associated with another embodiment or figure although not specifically described or shown as such.

It will be understood that, when a feature or element is referred to as being "connected", "attached", "coupled" or "responsive" to another feature or element, it can be directly connected, attached, coupled or responsive to the other feature or element or intervening features or elements may be present. In contrast, when a feature or element is referred to as being "directly connected", "directly attached", "directly coupled" or "directly responsive" to another feature or element, there are no intervening features or elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "headset" includes any type of device or earpiece that may be attached to or near the ear (or ears) of a user and may have various configurations, without limitation. Headsets as described herein may include mono headsets (one earbud) and stereo headsets (two earbuds), earbuds, hearing aids, ear jewelry, face masks, headbands, and the like.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of embodiments of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) who may wear a headset incorporating embodiments of the present invention.

In the included figures, various embodiments will be illustrated and described. However, it is to be understood that embodiments of the present invention are not limited to those worn by humans.

The ear is an ideal location for wearable health and environmental monitors. The ear is a relatively immobile platform that does not obstruct a person's movement or vision. Headsets located at an ear have, for example, access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Wireless, Bluetooth®-enabled, and/or other personal communication headsets may be configured to incorporate physiological and/or environmental sensors, according to some embodiments of the present invention. As a specific example, Bluetooth® headsets are typically lightweight, unobtrusive devices that have become widely accepted socially. Moreover, Bluetooth® headsets are cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance. Exemplary physiological and environmental sensors that may be incorporated into a Bluetooth® or other type of headsets include, but are not limited to accelerometers, auscultatory sensors, pressure sensors, humidity sensors, color sensors, light intensity sensors, pressure sensors, etc.

Optical coupling into the blood vessels of the ear may vary between individuals. As used herein, the term "coupling" refers to the interaction or communication between excitation light entering a region and the region itself. For example, one form of optical coupling may be the interaction between excitation light generated from within a light-guiding earbud and the blood vessels of the ear. Light guiding earbuds are described in co-pending U.S. Patent Application Publication No. 2010/0217102, which is incorporated herein by reference in its entirety. In one embodiment, this interaction may involve excitation light entering the ear region and scattering from a blood vessel in the ear such that the intensity of scattered light is proportional to blood flow within the blood vessel. Another form of optical coupling may be the interaction between excitation light generated by an optical emitter within an earbud and the light-guiding region of the earbud.

Various embodiments described herein are not limited to headsets that communicate wirelessly. In some embodiments of the present invention, headsets configured to monitor an individual's physiology and/or environment may be wired to a device that stores and/or processes data. In some embodiments, this information may be stored on the headset itself. Furthermore, various embodiments described herein are not limited to earbuds. Some embodiments may be employed around another part of the body, such as a digit, finger, toe, limb, wrist, around the nose or earlobe, or the like. Other embodiments may be integrated into a patch, such as a bandage that sticks on a person's body.

Photoplethysmograph (PPG) sensors are widely used in physiological signal processing systems and methods to generate a physiological waveform. A PPG sensor is a device that measures the relative blood flow using an infrared or other light source that is transmitted through or reflected off tissue, detected by a photodetector and quantified. Less light is absorbed when blood flow is greater, increasing the intensity of light reaching the detector. A PPG sensor can measure blood volume pulse, which is the phasic change in blood volume with each heartbeat. A PPG sensor can also measure heart rate, heart rate variability and/or other physiological metrics. Moreover, many other types of sensors may also be used in physiological signal processing systems described herein.

Unfortunately, these sensors may be highly sensitive to noise. When used with a portable physiological signal processing system/method, these sensors may be particularly susceptible to motion noise. Moreover, a PPG sensor also may be particularly sensitive to "sunlight interference", which may occur, for example, when a user is running beneath trees.

Averaging measurements may be used to reduce noise. Accordingly, many digital signal processing systems, and in particular physiological signal processing systems, may include an averager, such as an averaging filter or a spectral transform that effectively averages the response over a window of samples. The window function defines an impulse response. For example, when a filter is applied to a sequence of samples (either direct sensor samples or processed sensor samples), this may provide a weighted average of present and past samples, which may be specified as an impulse response. More broadly stated, an impulse response of a dynamic system represents its output when presented with a brief input signal called an "impulse". The impulse response may be used to fully characterize the operation of a dynamic system on an input signal, so that it may be used to represent a weighted or unweighted average of a variable number of samples, also referred to as a "sampling window size".

The selection of an impulse response for an averager can present a dilemma for the designer of a physiological signal processing system. In particular, there is a tradeoff between the window size versus the resolution of temporal changes of the measurement. Moreover, there is an inverse relationship between temporal resolution and frequency resolution.

Various embodiments described herein may arise from recognition that a desired or optimum tradeoff may vary with the nature of the noise. Pursuant to this recognition, various embodiments described herein can vary the averaging in time for physiological metric estimation based on conditions that set the noise. Thus, various embodiments described herein can provide a physiological metric extractor for a physiological waveform that is generated by a PPG sensor or other physiological sensor, wherein the physiological metric extractor includes an averager having an impulse response that is responsive to a motion signal that is generated by an inertial sensor. By being responsive to the motion signal, a smaller sampling window may be provided for low strength motion signals (for example, the subject at rest), whereas a larger sample window can be provided for a higher strength motion signal (for example, the subject in motion). Thus, higher resolution and higher noise rejection may be obtained, regardless of the presence of motion or other noise.

FIG. 1 is a functional block diagram of physiological signal processing systems and methods according to various embodiments described herein. Referring now to FIG. 1, these physiological signal processing systems/methods 100 may be used to process a physiological waveform 112 that is produced by a physiological sensor, such as a PPG sensor 110. The PPG sensor 110 generates an electrical physiological waveform. However, other physiological sensors may be provided to generate a physiological waveform that may include an electrical physiological waveform including an electroencephalogram (EEG), an electrocardiogram (ECG) and/or a radio frequency (RF) waveform, an electro-optical physiological waveform, an electro-photoacoustic waveform including a photoacoustic waveform, an electro-mechanical physiological waveform including an auscultation waveform, a piezo sensor waveform and/or an accelerometer waveform, and/or an electro-nuclear physiological waveform. When a PPG sensor 110 is used, the physiological waveform 112 may include both cardiovascular and pulmonary signal components therein.

Still referring to FIG. 1, a physiological metric extractor 130 extracts the physiological metric 132 from the physiological waveform 112. When a PPG sensor is used, the physiological metric 132 may include a heart rate, respiration rate, heart rate variability (HRV), pulse pressure, systolic blood pressure, diastolic blood pressure, step rate, oxygen uptake ($VO_2$), maximal oxygen uptake ($VO_2$ max), calories burned, trauma, cardiac output and/or blood analyte levels including percentage of hemoglobin binding sites occupied by oxygen ($SPO_2$), percentage of methemoglobins, percentage of carbonyl hemoglobin and/or glucose level. The physiological metric extractor 130 may extract the physiological metric 132 using one or more conventional techniques. Moreover, a physiological metric assessor 150 may be provided to extract a metric according to one or many known physiological metric assessment techniques. The physiological assessment may include ventilatory threshold, lactate threshold, cardiopulmonary status, neurological status, aerobic capacity ($VO_2$ max) and/or overall health or fitness.

Still referring to FIG. 1, the physiological metric extractor 130 may include an averager 120. The averager is configured to obtain an average of the physiological waveform 112. It will be understood that the physiological waveform 112 may be directly averaged, or the physiological waveform 112 may be processed and/or conditioned prior to averaging by the averager 120. The averager 120 may operate in the time domain or in the frequency domain. The operation of the averager 120 defines an impulse response. For example, when the averager 120 provides a weighted average response over a window of samples that are derived from the physiological waveform 112, the weights and the number of samples in the window define the impulse response of the averager.

According to various embodiments described herein, the impulse response of the averager 120 is responsive to a motion signal, and in some embodiments a strength of a motion signal. For example, referring again to FIG. 1, an inertial sensor 140 may be provided to generate a motion signal 142. The inertial sensor 140 may comprise an accelerometer, an optical sensor, a blocked channel sensor, a capacitive sensor and/or a piezo sensor. A blocked channel sensor is described, for example, in U.S. Patent Application Publication No. 2010/0217102 to LeBoeuf et al. entitled Light-Guiding Devices and Monitoring Devices Incorporating Same, the disclosure of which is hereby incorporated herein by reference as if set forth fully herein. The inertial sensor 140 generates a motion signal 142. In some embodiments, the motion signal 142 is applied to a motion signal strength determiner 160 that provides a motion signal strength 162 to the averager 120. The motion signal strength determiner 160 may determine the motion signal strength 162 as a maximum, sum of squares, maximum of squares, sum of absolute values, maximum of absolute values, root-sum-squares, root-mean-squares and/or decimation of a magnitude of the motion signal over a given time interval.

Finally, one or more of the elements illustrated in FIG. 1 may be included in a portable housing 170 along with a power supply, such as a battery and/or capacitor power supply for the components in the housing 170. An example of such a housing is described, for example, in U.S. Patent Application Publication 2010/0217098 to LeBoeuf et al. entitled Form-Fitted Monitoring Apparatus for Health and Environmental Monitoring, the disclosure of which is hereby incorporated herein by reference as if set forth fully herein. However, in other embodiments, one or more of the elements of FIG. 1 may be external to the housing 170. For example, the PPG sensor 110, the inertial sensor 140, the motion signal strength determiner 160 and/or the physiological metric assessor 150 may be external to the housing 170.

It will also be understood that the averager 120 is functionally illustrated in FIG. 1 as being within the functional block of the physiological metric extractor 130. However, the averager 120 may be physically separate from the physiological metric extractor 130, so that the averager 120 operates on the physiological waveform 112 before it enters the physiological metric extractor 130, to provide an average of the physiological waveform 112 over a given time interval, and provides this average to the physiological metric extractor 130. For example, the averager may be included in an output buffer of the PPG sensor or provided as a separate interface between the PPG sensor 110 and the physiological metric extractor 130. Functionally, however, the averager 120 may be regarded as being included in physiological metric extraction, regardless of its physical location.

FIG. 1 also illustrates physiological signal processing systems according to various other embodiments described herein for a physiological waveform 112 that is generated by a PPG sensor 110 and a motion signal 142, wherein these physiological signal processing systems include a physiological metric extractor 130 that is configured to extract a physiological metric 132 from the physiological waveform 112 that is generated by the PPG sensor 110. The physiological metric extractor includes an averager 120 having an averaging window size that is responsive to the motion signal 142. FIG. 1 also illustrates physiological signal processing methods according to various embodiments described herein that comprise setting an impulse response in response to a motion signal 142, averaging a physiological waveform 112 that is generated by a PPG sensor 110 based on the impulse response that was set, and extracting a physiological metric 132 from the physiological waveform that was averaged. FIG. 1 also describes physiological signal processing methods according to various embodiments described herein that comprise setting an averaging window size in response to a motion signal 142, averaging a physiological waveform that is generated by a PPG sensor 110 based on the averaging window size that was set, and extracting a physiological metric 132 from the physiological waveform that was averaged.

Figure 2:
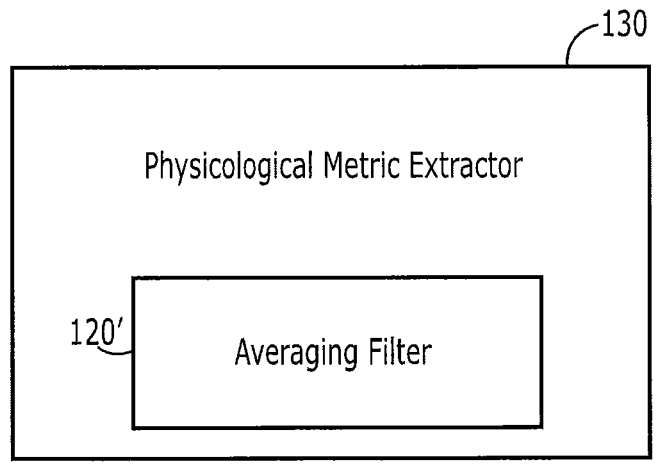
FIGS. 2-4 are functional block diagrams of physiological metric extractors according to various embodiments described herein.
Figure 3:
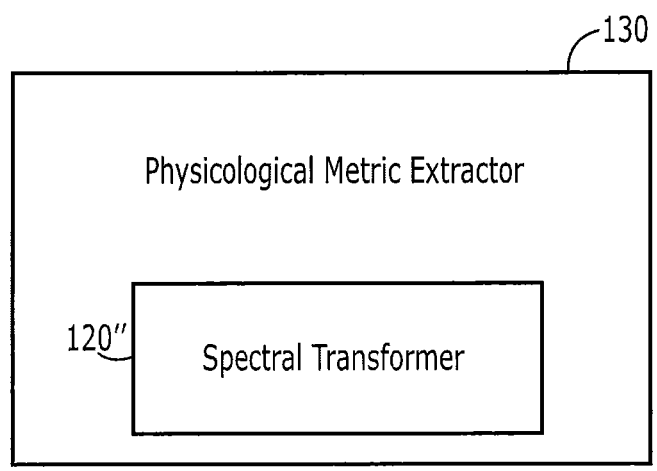
Figure 4:
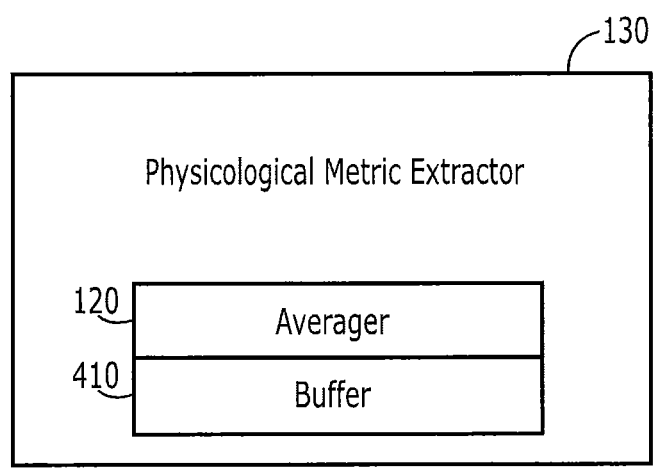

The averager 120 may be embodied in many forms, as illustrated in FIGS. 2-4. For example, in FIG. 2, the averager 120 may be embodied by an averaging filter 120', which provides a weighted average of samples of the physiological waveform 112. In these embodiments, both the weights and the number of samples in a sampling window can define an impulse response, and are responsive to the motion signal 142. In FIG. 3, the averager 120 is embodied by a spectral transformer 120" that is configured to provide a weighted average spectral response over a window of samples that are derived from the physiological waveform 112 that is generated by the PPG sensor 110, wherein the weights and the number of samples in the window of samples define the impulse response. Finally, in FIG. 4, the physiological metric extractor 130 may further comprise a buffer 410 that is configured to store a plurality of processed or unprocessed samples of the physiological waveform 112 therein, ranging from a newest sample to the oldest sample. The buffer 410 may be configured to store sufficient samples to correspond to a largest desired averaging window size. Many other examples of averagers 120 may also be provided.

As was described in connection with FIG. 1, the averager 120 has an impulse response that is responsive to the motion signal 142 and, in some embodiments, to the motion signal strength 162. The impulse response may a linear, nonlinear, discrete and/or continuous function of the strength of the motion signal. Various examples will now be described wherein it is assumed that the averager 120 operates in the time domain, and wherein a window size of a moving average of the averager 120 defines the impulse response. Thus, in the embodiments that will now be described, the window size of the moving average of the averager 120 is a linear, nonlinear, discrete and/or continuous function of the strength of the motion signal 162. It will be understood, however, that the averager 120 may operate in the frequency domain, and that the impulse response of the averager 120 may be defined by a window size and a weight that is applied to each of the samples and/or using other techniques.

Figure 5:
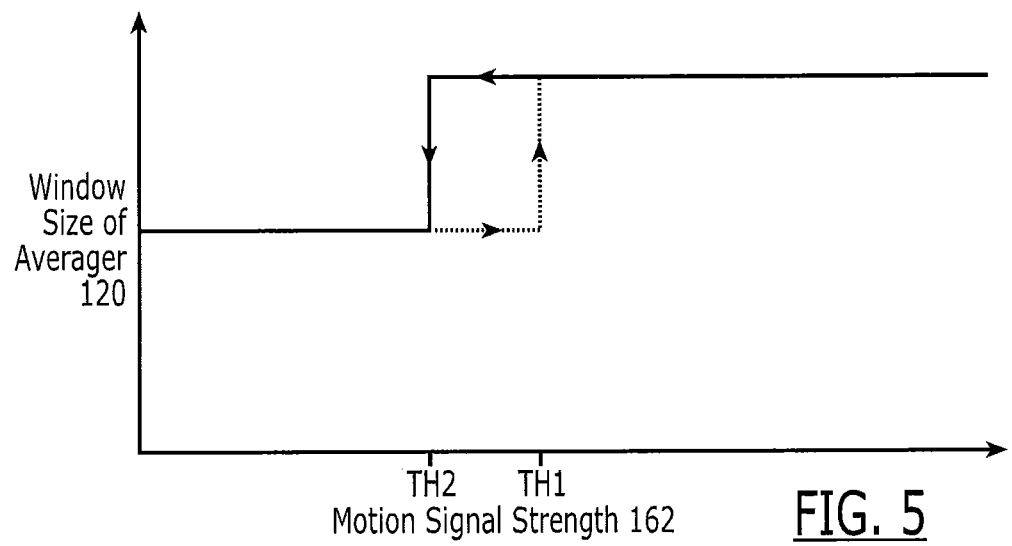
FIGS. 5-8 graphically illustrate various window sizes of an averager as a function of motion signal strength according to various embodiments described herein.

For example, FIG. 5 graphically illustrates a window size of the averager 120 relative to motion signal strength 162. As shown in FIG. 5, a first averaging window size is provided in response to the motion signal strength 162 exceeding a first threshold TH1 and a second value of the window size of the averager 120 is provided in response to the strength of the motion signal 162 being less than a second threshold TH2. It will be understood that the first and second thresholds may be the same in some embodiments. In other embodiments, different thresholds may be used, as shown in FIG. 5, to provide hysteresis and reduce the likelihood of rapid switching of window size when the motion signal value is in the vicinity of the thresholds. In one example, a six second sampling interval (averaging window size) may be provided when the motion signal strength is below a given threshold and a ten second sampling interval (averaging window size) may be provided when the motion signal strength is above a given threshold. These examples will be illustrated below with actual data. Accordingly, FIG. 5 illustrates various embodiments wherein the impulse response has a first value in response to the strength of the motion signal exceeding a first threshold, and a second value in response to the strength of the motion signal being less than a second threshold.

Thus, a simple form of various embodiments described herein uses a motion flag, where motion is declared when the accelerometer strength is greater than a predetermined threshold, and where rest is otherwise declared. The motion flag then determines which of two predetermined window sizes are used for a spectral transform. A more complex form can map the accelerometer strength to multiple window sizes and/or further characteristics, as will be described in connection with FIGS. 6-8 below.

Figure 6:
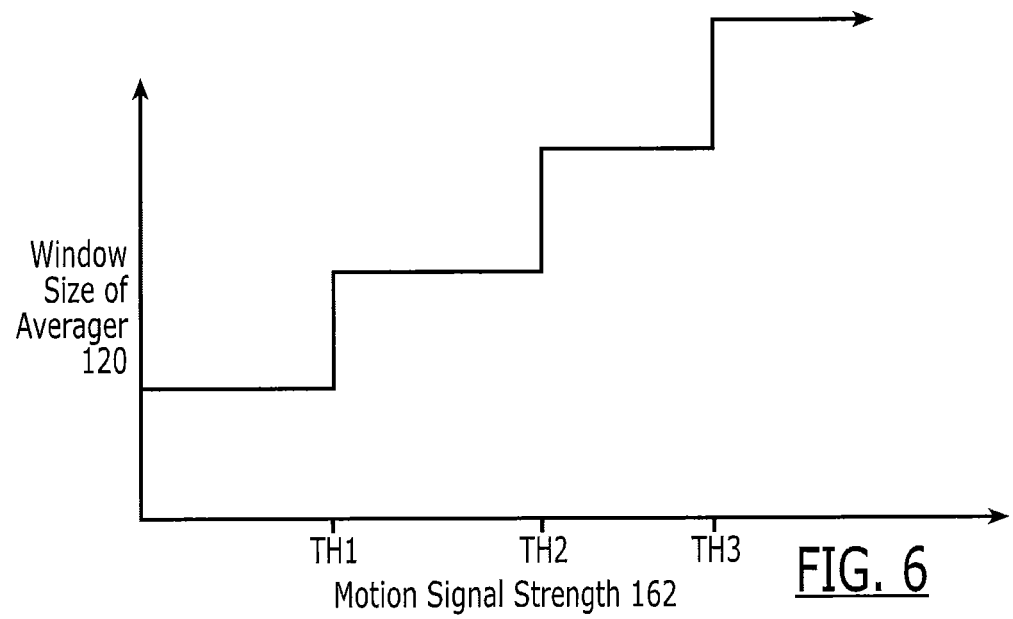

More than two thresholds may be used, as illustrated in FIG. 6. For example, FIG. 6 illustrates that the impulse response has a first value that sets a first averaging window size of the averager in response to the strength of the motion signal exceeding the first threshold TH1, but being less than the second threshold TH2, a second value that sets a second averaging window size of the averager in response to the strength of the motion signal exceeding the second threshold TH2, but being less than a third threshold TH3, and a third value that sets a third averaging window size of the averager in response to the strengths of the motion signal exceeding the third threshold TH3. In one specific example, the averaging window size may be four, seven or ten seconds long in response to the three different threshold ranges that are defined. It will be understood that more than three thresholds may be used, and that hysteresis may also be used.

Figure 7:
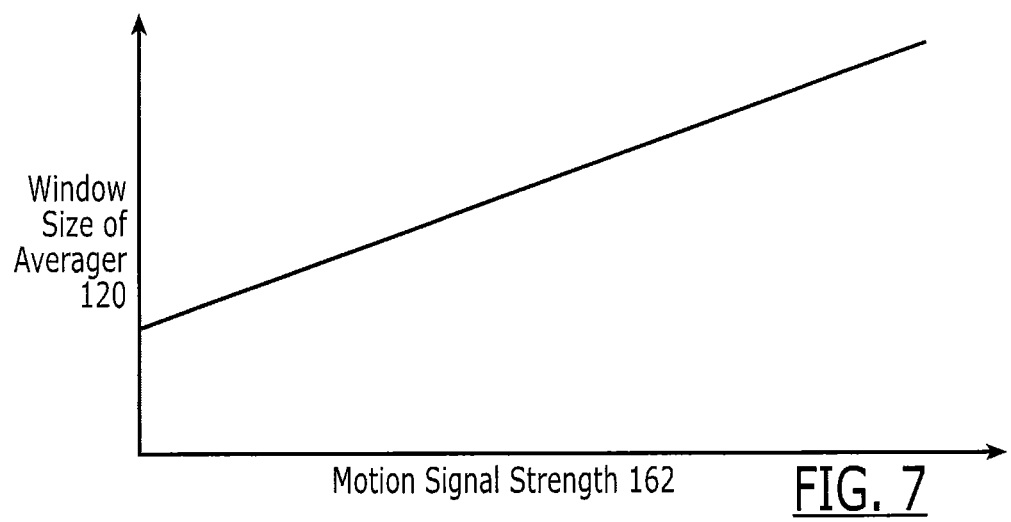
Figure 8:
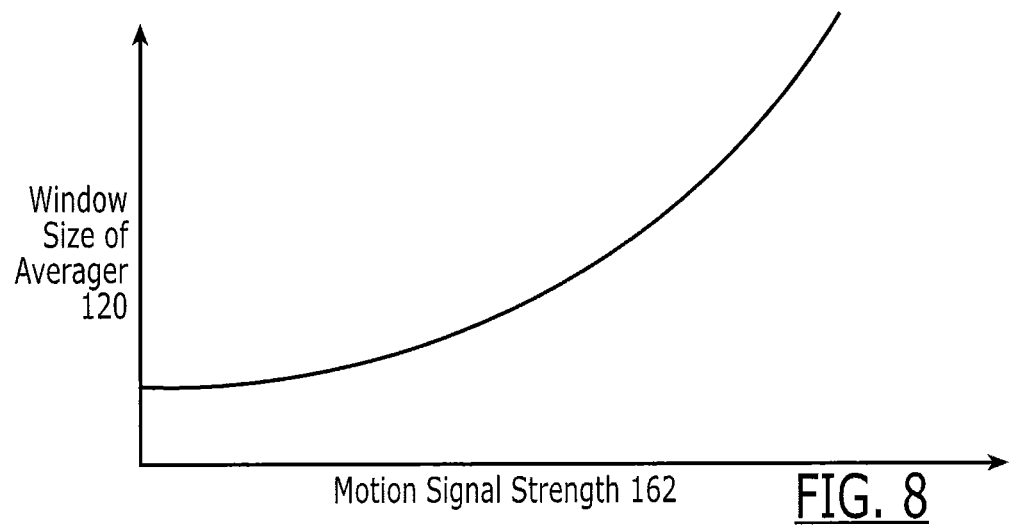

FIG. 7 illustrates other embodiments wherein the averaging window size of the averager is a linear function of a strength of the motion signal. Specifically, in FIG. 7, the averaging window size increases linearly with the strength of the motion signal. FIG. 8 illustrates other embodiments wherein the averaging window size of the averager is a nonlinear function, such as a parabolic function, of the strength of the motion signal. Thus, in FIG. 8, the window size increases parabolically with the strength of the motion signal. Various other linear and/or nonlinear functions may be employed and the various functions of FIGS. 5-8 may also be combined in various combinations and subcombinations.

It will be understood that in any of the embodiments described herein, it may be desirable to avoid discontinuities when changing averaging window sizes. Accordingly, it may be desirable to use a delay line or a buffer corresponding to the largest anticipated window size, and allow the smaller window to encompass the newest samples in the delay line.

Discontinuity may thereby be reduced or minimized. Hysteresis, as was described in FIG. 5, may also reduce discontinuity.

Figure 9:
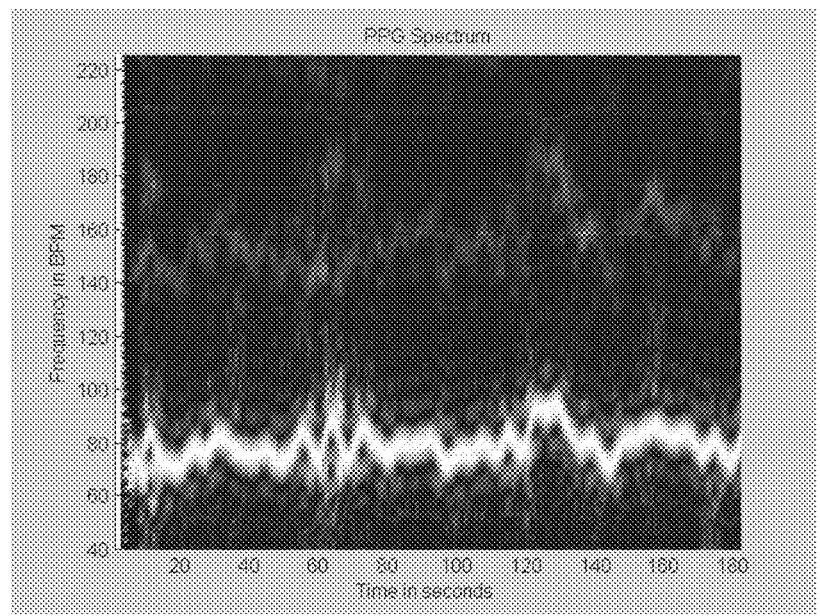
FIGS. 9-14 illustrate waveform spectra according to various embodiments described herein.
Figure 10:
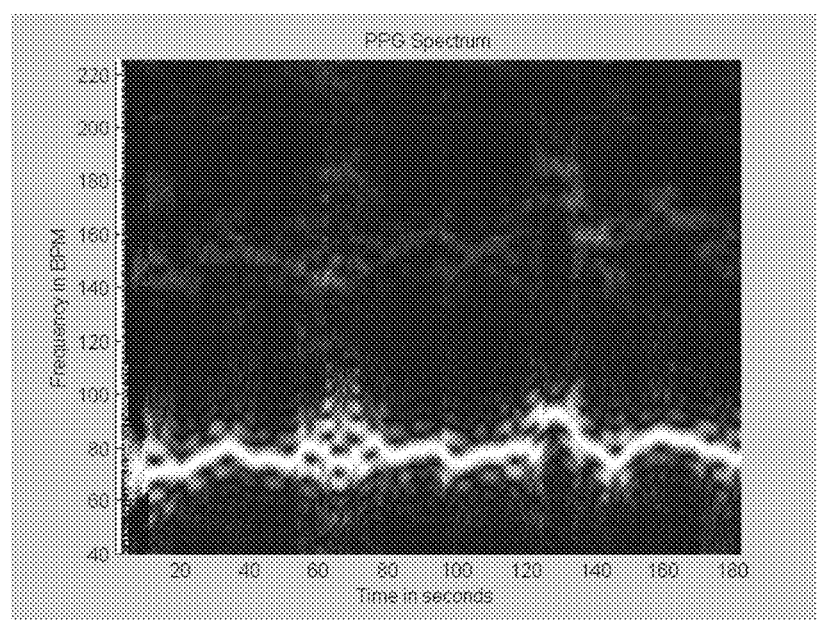

FIGS. 9-14 are oscillographs of spectra of a physiological metric 132 (here, heart rate in beats per minute (BPM)) over time, based on a physiological waveform 112 from a PPG sensor 110 that is processed by a physiological metric extractor 130 including a spectral transformer 120" having a sampling window in the time domain of six seconds or ten seconds. Specifically, FIG. 9 illustrates a subject at rest, so that the motion signal strength 162 is low, and a six second spectral transform window is applied. FIG. 10 illustrates a subject at rest with a ten second spectral transform window. Comparing FIGS. 9 and 10, it can be seen that a six second window resolves the physiological waveform more clearly than the ten second window. Compare, for example, the physiological waveform at about 60 seconds, which is clearly resolvable in FIG. 9, but not clearly resolvable in FIG. 10. Accordingly, for a subject at rest (low motion signal strength 162), a smaller averaging window provides greater agility in tracking the dynamic heart rate with a six second spectral transform window.

Figure 11:
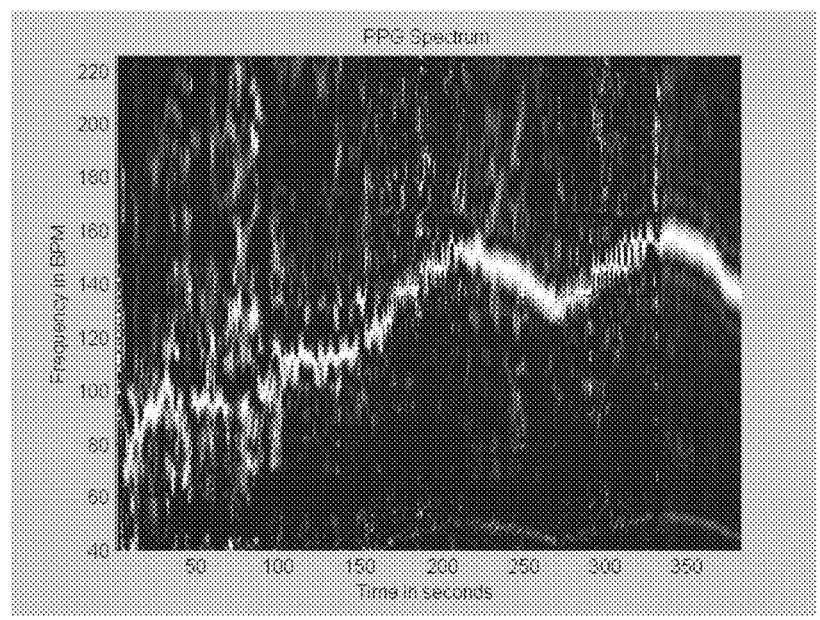
Figure 12:
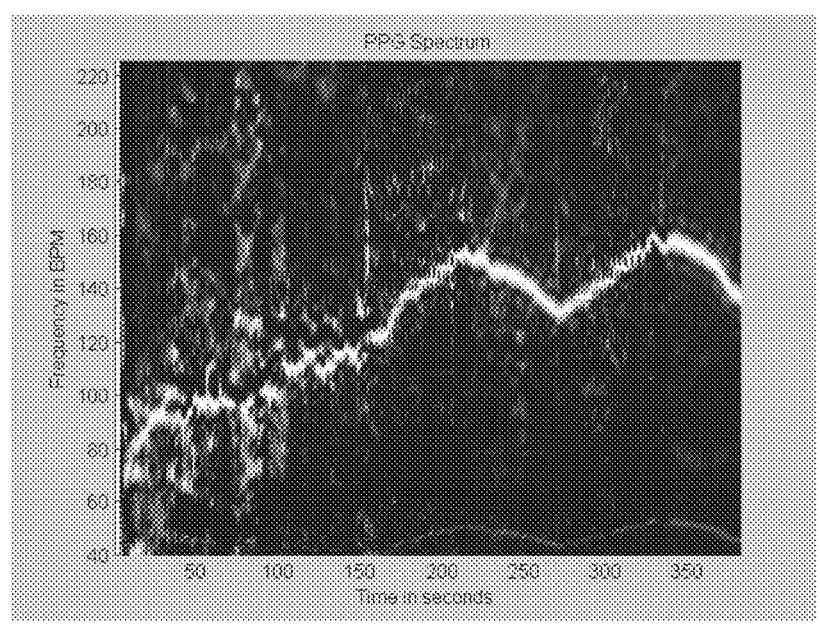

Now compare FIGS. 11 and 12, which both illustrate a subject in motion (motion signal strength 162 high). FIG. 11 uses a six second spectral transform window, whereas FIG. 12 uses a ten second spectral transform window. Comparing FIGS. 11 and 12, the physiological waveform 112 is more resolvable using the larger sampling window of FIG. 12 than the smaller sampling window of FIG. 11. Compare the sharp or crisp signal in FIG. 12 to the fuzzy signal of FIG. 11, and the greater amount of noise of FIG. 11 compared to FIG. 12. Thus, for example, when running, a sharper signal is obtained and less noise is obtained when using a larger sampling window of FIG. 12 compared to the smaller sampling window of FIG. 11.

Figure 13:
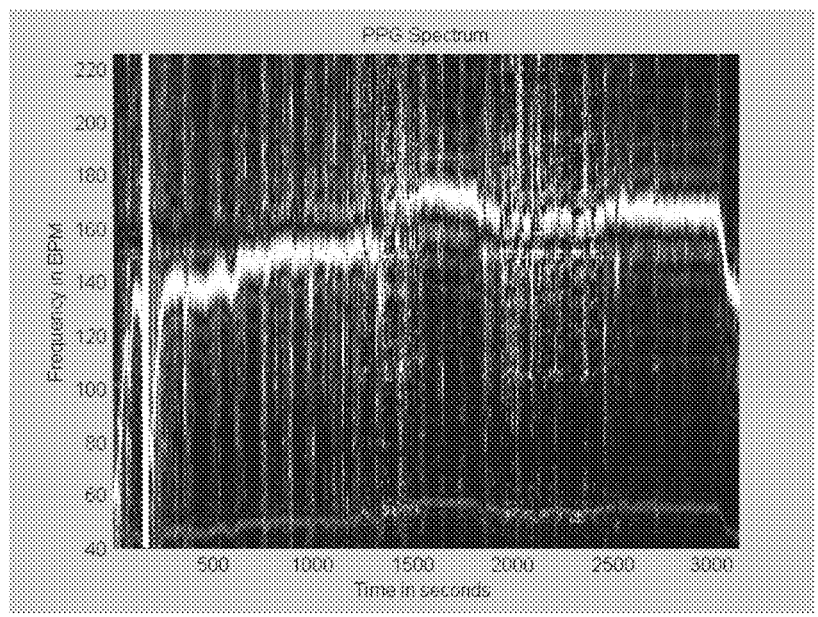
Figure 14:
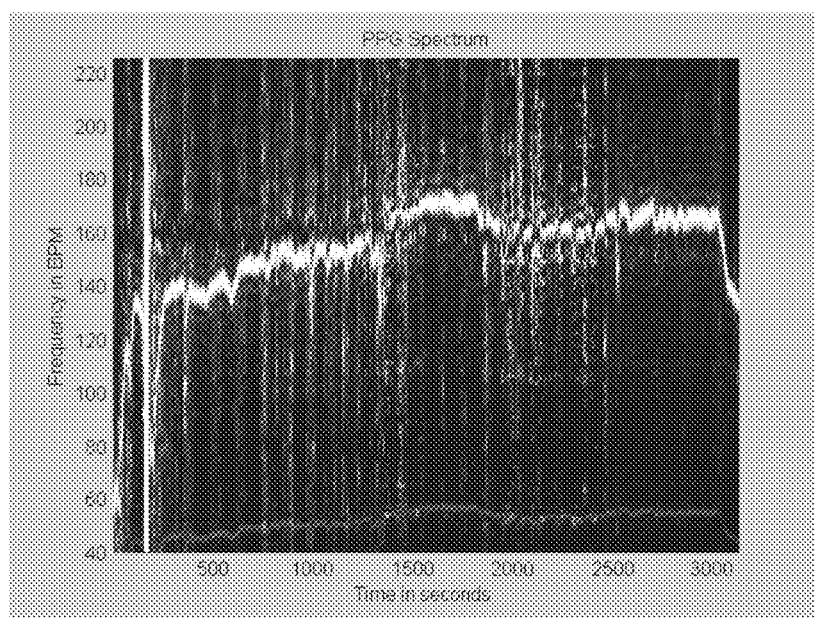

Finally, FIGS. 13 and 14 compare a subject in motion with "sunlight interference". Sunlight interference refers to interference in an optical signal, such as a PPG signal, when a user is running beneath trees on a sunny day. A six second spectral transform window is used in FIG. 13 and a ten second spectral transform window is used in FIG. 14. As with FIGS. 11 and 12, the larger spectral transform window of FIG. 14 provides a more resolvable signal in the presence of motion and in the presence of sunlight interference, compared to FIG. 13. Compare the sharper signal in FIG. 14 with the fuzzy signal in FIG. 13, and the lower amount of background noise in FIG. 14 with the higher amount of background noise in FIG. 13. Thus, FIG. 14 illustrates an unexpected potential benefit of various embodiments described herein, which may provide reduced sunlight interference sensitivity as well. Accordingly, a runner running indoors may obtain a more accurate physiological metric using various embodiments described herein, and a runner running outdoors subject to sunlight interference may obtain an added benefit when using various embodiments described herein.

Various embodiments have been described herein primarily with respect to physiological signal processing systems. However, FIGS. 1-8 also illustrate analogous physical signal processing methods according to various embodiments described herein.

Various embodiments have been described herein with reference to block diagrams of methods, apparatus (systems and/or devices) and/or computer program products. It is understood that a block of the block diagrams, and combinations of blocks in the block diagrams, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams, and thereby create means (functionality), structure and/or methods for implementing the functions/acts specified in the block diagrams.

These computer program instructions may also be stored in a computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-ray™).

The computer program instructions may also be loaded onto a computer and/or other programmable data processing apparatus to cause a series of operational steps to be performed on the computer and/or other programmable apparatus to produce a computer-implemented process or method such that the instructions which execute on the computer or other programmable apparatus provide steps for implementing the functions/acts specified in the block diagrams.

Accordingly, the invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the blocks. For example, two blocks shown in succession may in fact be executed substantially concurrently or the blocks may sometimes be executed in the reverse order, depending upon the functionality/acts involved. Moreover, the functionality of a given block of the block diagrams may be separated into multiple blocks and/or the functionality of two or more blocks of the block diagrams may be at least partially integrated. Finally, other blocks may be added/inserted between the blocks that are illustrated.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of all combinations and subcombinations of the embodiments described herein, and of the manner and process of making and using them, and shall support claims to any such combination or subcombination.

In the drawings and specification, there have been disclosed embodiments of the invention and, although specific terms are employed, they are used in a generic and descriptive sense only and not for purposes of limitation, the scope of the invention being set forth in the following claims.

What is claimed is:

1. A physiological signal processing system comprising:
   a photoplethysmograph (PPG) sensor that is configured to generate a physiological waveform;
   an inertial sensor that is configured to generate a motion signal; and
   physiological metric extractor circuitry that is configured to extract a physiological metric from the physiological waveform that is generated by the PPG sensor,
   wherein the physiological metric extractor circuitry is further configured to extract the physiological metric using an averager having an impulse response defined by an averaging window size,
   wherein the averaging window size is defined in a time domain and is responsive to a strength of the motion signal, and wherein the averaging window size is increased or decreased with increases or decreases in the strength of the motion signal, respectively.

2. A physiological signal processing system according to claim 1:
   wherein the strength of the motion signal comprises a maximum, sum of squares, maximum of squares, sum of absolute values, maximum of absolute values, root-sum-squares, root-mean-squares and/or decimation of a magnitude of the motion signal over a given time interval; or
   wherein the impulse response has a first value in response to the strength of the motion signal exceeding a first threshold and a second value in response to the strength of the motion signal being less than a second threshold, and wherein the first value of the impulse response sets a first averaging window size of the averager and the second value of the impulse response sets a second averaging window size of the averager; or
   wherein the averaging window size of the averager is a mathematical function of the strength of the motion signal.

3. A physiological signal processing system according to claim 1, wherein the impulse response has a first value in response to the strength of the motion signal exceeding a first threshold but being less than a second threshold, a second value in response to the strength of the motion signal exceeding the second threshold but being less than a third threshold and a third value in response to the strength of the motion signal exceeding the third threshold,
   wherein the first value of the impulse response sets a first averaging window size of the averager, the second value of the impulse response sets a second averaging window size of the averager and the third value of the impulse response sets a third averaging window size of the averager.

4. A physiological signal processing system for a motion signal and a physiological waveform that is generated by a photoplethysmograph (PPG) sensor, the physiological signal processing system comprising:
   physiological metric extractor circuitry that is configured to extract a physiological metric from the physiological waveform that is generated by the PPG sensor,
   wherein the physiological metric extractor circuitry is further configured to extract the physiological metric using an averager having an averaging window size that is defined in a time domain and is responsive to a strength of the motion signal, and wherein the averaging window size is increased or decreased with increases or decreases in the strength of the motion signal, respectively.

5. A physiological signal processing system according to claim 4:
   wherein the strength of the motion signal comprises a maximum, sum of squares, maximum of squares, sum of absolute values, maximum of absolute values, root-sum-squares, root-mean-squares and/or decimation of a magnitude of the motion signal over a given time interval; or
   wherein the averaging window size has a first value in response to the strength of the motion signal exceeding a first threshold and a second value in response to the strength of the motion signal being less than a second threshold; or
   wherein the averaging window size is a mathematical function of the strength of the motion signal.

6. A physiological signal processing method comprising:
   setting an impulse response defined by an averaging window size, wherein the averaging window size is defined in a time domain and is set in response to a strength of a motion signal;
   averaging a physiological waveform that is generated by a photoplethysmograph (PPG) sensor based on the impulse response that was set; and
   extracting a physiological metric from the physiological waveform that was averaged,
   wherein the averaging window size is increased or decreased with increases or decreases in the strength of the motion signal, respectively.

7. A physiological signal processing method according to claim 6:
   wherein the strength of the motion signal comprises a maximum, sum of squares, maximum of squares, sum of absolute values, maximum of absolute values, root-sum-squares, root-mean-squares and/or decimation of a magnitude of the motion signal over a given time interval; or
   wherein the impulse response has a first value in response to the strength of the motion signal exceeding a first threshold and a second value in response to the strength of the motion signal being less than a second threshold, and wherein the first value of the impulse response sets a first averaging window size of the averaging and the second value of the impulse response sets a second averaging window size of the averaging.

8. A physiological signal processing method according to claim 6:
   wherein the physiological metric comprises a heart rate, respiration rate, heart rate variability (HRV), pulse pressure, systolic blood pressure, diastolic blood pressure, step rate, oxygen uptake ($VO_2$), maximal oxygen uptake ($VO_2$ max), calories burned, trauma, cardiac output and/or blood analyte levels including percentage of hemoglobin binding sites occupied by oxygen ($SPO_2$), percentage of methemoglobins, percentage of carbonyl hemoglobin and/or glucose level.

9. A physiological signal processing method according to claim 6 further comprising:
   processing the physiological metric to generate at-least-one physiological assessment,
   wherein the at-least-one physiological assessment includes ventilatory threshold, lactate threshold, cardiopulmonary status, neurological status, aerobic capacity ($VO_2$ max) and/or overall health or fitness.

10. The physiological signal processing method according to claim 6, wherein the averaging window size has a first time duration in response to the strength of the motion signal exceeding a first threshold, and a second time duration, different than the first time duration, in response to the strength of the motion signal being less than a second threshold.

11. A physiological signal processing method comprising:
setting an averaging window size, wherein the averaging window size is defined in a time domain and is set in response to a strength of a motion signal;
averaging a physiological waveform that is generated by a photoplethysmograph (PPG) sensor based on the averaging window size that was set; and
extracting a physiological metric from the physiological waveform that was averaged,
wherein the averaging window size has a first time duration in response to the strength of the motion signal exceeding a first threshold, and a second time duration, different than the first time duration, in response to the strength of the motion signal being less than a second threshold.

12. A physiological signal processing method according to claim 11:
wherein the strength of the motion signal comprises a maximum, sum of squares, maximum of squares, sum of absolute values, maximum of absolute values, root-sum-squares, root-mean-squares and/or decimation of a magnitude of the motion signal over a given time interval; or
wherein the averaging window size is a mathematical function of the strength of the motion signal.

13. A physiological signal processing method according to claim 11 wherein the physiological metric comprises a heart rate, respiration rate, heart rate variability (HRV), pulse pressure, systolic blood pressure, diastolic blood pressure, step rate, oxygen uptake ($VO_2$), maximal oxygen uptake ($VO_2$ max), calories burned, trauma, cardiac output and/or blood analyte levels including percentage of hemoglobin binding sites occupied by oxygen ($SPO_2$), percentage of methemoglobins, percentage of carbonyl hemoglobin and/or glucose level.

14. A physiological signal processing method according to claim 11 further comprising:
processing the physiological metric to generate at-least-one physiological assessment,
wherein the at-least-one physiological assessment includes ventilatory threshold, lactate threshold, cardiopulmonary status, neurological status, aerobic capacity ($VO_2$ max) and/or overall health or fitness.

15. A physiological signal processing method according to claim 11, wherein the second threshold is different than the first threshold.

16. A physiological signal processing system comprising:
a photoplethysmograph (PPG) sensor that is configured to generate a physiological waveform;
an inertial sensor that is configured to generate a motion signal; and
physiological metric extractor circuitry that is configured to extract a physiological metric from the physiological waveform that is generated by the PPG sensor,
wherein the physiological metric extractor circuitry is further configured to extract the physiological metric using an averager having an impulse response defined by an averaging window size,
wherein the averaging window size is defined in a time domain and is responsive to a strength of the motion signal, and
wherein the averaging window size has a first time duration in response to the strength of the motion signal exceeding a first threshold, and a second time duration, different than the first time duration, in response to the strength of the motion signal being less than a second threshold.

17. A physiological signal processing system according to claim 16, wherein the physiological metric extractor circuitry further comprises a spectral transformer that is configured to provide a weighted average spectral response over a window of samples that are derived from the physiological waveform that is generated by the PPG sensor, wherein weights and a number of samples in the window of samples define the impulse response.

18. A physiological signal processing system according to claim 16, wherein the physiological metric extractor circuitry further comprises a buffer configured to store a plurality of samples of the physiological waveform that is generated by the PPG sensor therein, ranging from a newest sample to an oldest sample, and wherein the buffer is further configured to store sufficient samples to correspond to a largest value of the averaging window size.

19. A physiological signal processing system according to claim 16:
wherein the inertial sensor comprises an accelerometer, an optical sensor, a blocked channel sensor, a capacitive sensor and/or a piezo sensor; or
wherein the physiological metric comprises a heart rate, respiration rate, heart rate variability (HRV), pulse pressure, systolic blood pressure, diastolic blood pressure, step rate, oxygen uptake ($VO_2$), maximal oxygen uptake ($VO_2$ max), calories burned, trauma, cardiac output and/or blood analyte levels including percentage of hemoglobin binding sites occupied by oxygen ($SPO_2$), percentage of methemoglobins, percentage of carbonyl hemoglobin and/or glucose level; or
further comprising a portable housing, wherein the PPG sensor, the inertial sensor and the physiological metric extractor circuitry are all included in the portable housing.

20. A physiological signal processing system according to claim 16, further comprising:
physiological metric assessor circuitry that is responsive to the physiological metric extractor circuitry and that is configured to process the physiological metric to generate at-least-one physiological assessment,
wherein the at-least-one physiological assessment includes ventilatory threshold, lactate threshold, cardiopulmonary status, neurological status, aerobic capacity ($VO_2$ max) and/or overall health or fitness.

21. A physiological signal processing system according to claim 16, wherein the averaging window size is increased or decreased with increases or decreases in the strength of the motion signal, respectively.

22. A physiological signal processing system according to claim 16, wherein the second threshold is different than the first threshold.

23. A physiological signal processing system for a motion signal and a physiological waveform that is generated by a photoplethysmograph (PPG) sensor, the physiological signal processing system comprising:
physiological metric extractor circuitry that is configured to extract a physiological metric from the physiological waveform that is generated by the PPG sensor, wherein the physiological metric extractor circuitry is further configured to extract the physiological metric using an averager having an averaging window size that is defined in a time domain and is responsive to a strength of the motion signal, and wherein the averaging window size has a first time duration in response to the strength of the motion signal exceeding a first threshold and a second time duration, different than the first time duration, in response to the strength of the motion signal being less than a second threshold.

24. A physiological signal processing system according to claim 23:

wherein the physiological metric extractor circuitry further comprises a buffer configured to store a plurality of samples of the physiological waveform that is generated by the PPG sensor therein, ranging from a newest sample to an oldest sample, and wherein the buffer is further configured to store sufficient samples to correspond to a largest value of the averaging window size; or wherein the physiological metric comprises a heart rate, respiration rate, heart rate variability (HRV), pulse pressure, systolic blood pressure, diastolic blood pressure, step rate, oxygen uptake ($VO_2$), maximal oxygen uptake ($VO_2$ max), calories burned, trauma, cardiac output and/or blood analyte levels including percentage of hemoglobin binding sites occupied by oxygen ($SPO_2$), percentage of methemoglobins, percentage of carbonyl hemoglobin and/or glucose level.

25. A physiological signal processing system according to claim 23, further comprising:

physiological metric assessor circuitry that is responsive to the physiological metric extractor circuitry and that is configured to process the physiological metric to generate at-least-one physiological assessment, wherein the at-least-one physiological assessment includes ventilatory threshold, lactate threshold, cardiopulmonary status, neurological status, aerobic capacity ($VO_2$ max) and/or overall health or fitness.

26. A physiological signal processing system according to claim 23, wherein the second threshold is different than the first threshold.

* * * * *